United States Patent
Golberg et al.

(10) Patent No.: US 9,395,266 B2
(45) Date of Patent: Jul. 19, 2016

(54) ON-TOOL WAVEFRONT ABERRATIONS MEASUREMENT SYSTEM AND METHOD (71) Applicant: APPLIED MATERIALS ISRAEL LTD., Rehovot (IL)

(72) Inventors: Boris Golberg, Ashod (IL); Amir Moshe Sagiv, Beit-Zayit (IL); Haim Feldman, Nof-Ayalon (IL); Uriel Malul, Nes-Ziona (IL); Adam Baer, Rehovot (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 112 days.

(21) Appl. No.: 14/560,932

(22) Filed: Dec. 4, 2014

(65) Prior Publication Data
US 2015/0300913 A1    Oct. 22, 2015

Related U.S. Application Data (60) Provisional application No. 61/912,411, filed on Dec. 5, 2013.

(51) Int. Cl.
G01M 11/00     (2006.01)
G01N 21/95     (2006.01)
G02B 21/12     (2006.01)

(52) U.S. Cl.
CPC ........... *G01M 11/00* (2013.01); *G01N 21/9501* (2013.01); *G02B 21/125* (2013.01)

(58) Field of Classification Search
USPC ......................................................... 356/124
See application file for complete search history.

(56) References Cited

U.S. PATENT DOCUMENTS

2005/0219515 A1* 10/2005 Morohoshi ............. G03F 7/706
                                                    356/124
2014/0139825 A1*  5/2014 Unno ................ G01M 11/0242
                                                    356/124

* cited by examiner

*Primary Examiner* — Kara E Geisel
*Assistant Examiner* — Amanda Merlino
(74) *Attorney, Agent, or Firm* — Kilpatrick Townsend & Stockton LLP (57) ABSTRACT An on-tool measurement system and a method for measuring optical system's wavefront (WF) aberrations are disclosed. The on-tool measurement system includes an optical setup comprising a moveable deflection element further comprising a highly transparent region. The deflection element includes a first surface configured to project a first image of at least one object onto a sensor and the highly transparent region includes a second surface configured to project a second image of the at least one object onto the sensor. The on-tool measurement system includes a sensor configured to capture the first and second images and a controller configured to measure differential displacements between the first and second images at each deflection element position and to calculate the optical setup local WF gradients that depend on the measured differential displacements.

15 Claims, 8 Drawing Sheets

ON-TOOL WAVEFRONT ABERRATIONS MEASUREMENT SYSTEM AND METHOD

CROSS-REFERENCES TO RELATED APPLICATIONS

This application claims the benefit of U.S. Provisional Application No. 61/912,411, filed on Dec. 5, 2013. The disclosure of which is hereby incorporated by reference in its entirety for all purposes.

FIELD OF THE INVENTION

The invention relates generally to optical system's wavefront aberrations and more particularly the invention relates to an on-tool wavefront aberrations measurement system and method.

BACKGROUND

Mask inspection systems disclosed for example in published US patent application 2003/0156280, US patent application 2003/0179369 and US patent application 2003/0148114, aim to increase throughput and sensitivity of inspection tools. Mask inspection systems may use deep ultraviolet (DUV) lasers, having a short wavelength of 266 nanometers (nm) for wafer inspection and 193 nm for mask inspection, for example, in order to increases resolution and sensitivity of defect detection where small size defects, smaller than 50 nm should be detected and marked as suspected defects by inspection tools.

Optical systems generate wavefront (WF) aberrations that may be characterized, for example, by a Shack-Hartmann wavefront sensor configured to measure localized slope of the wavefront using spot displacement in the sensor plane.

WF aberrations may cause false detections, and/or detection misses, in die-to-die or cell-to-cell comparisons, for example, where an inspection system is configured to compare two images, which are expected to be identical. Due to optical system's WF aberrations, inspection system may erroneously classify regular objects as suspected defects or miss classify suspected defects when such defects do exist.

WF aberrations reduce the optical system quality and hence reduce the ability to detect and characterize reliably small defects, <50 nm, using DUV lasers. Additionally, WF aberrations may vary between inspection tools' optical systems that hence may have different signal-to-noise (SNR) ratio that may reduce further the reliability of mask inspection tools.

Modern semiconductor process tools' optical systems, used in mask inspection and stepper tools, are inherently more sensitive to the optical system's WF aberrations due to the short wavelength DUV lasers used to detect nanoscale defects having less than 50 nm sizes.

It should be noted that while about a million suspected defect locations may be found per mask or wafer optical inspection, only a small portion of the suspected defect locations are true defects that would probably cause a yield reduction, and the bigger portion of the suspected defects are false detections that should be screened by inspection tools.

In view of the above, it would be desirable to provide an on-tool WF aberrations measurement systems and methods that will enable measuring and monitoring routinely WF aberrations of semiconductor process tools and further will allow compensating for the measured optical system's WF aberrations in order to increase process yields and reliability of inspection of semiconductor process tools.

The information included in this background section of the specification, including any reference cited herein and any description or discussion thereof, is included for technical reference purposes only and is not to be regarded as a subject matter by which the scope of the invention is to be bound.

SUMMARY

This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the aspects and features set forth above or described in detail below.

In a first aspect, an on-tool measurement system for measuring optical system's wavefront (WF) aberrations is provided. The on-tool measurement system includes an optical setup comprising a moveable deflection element further comprising a highly transparent region. The deflection element includes a first surface configured to project a first image of at least one object onto a sensor and the highly transparent region includes a second surface configured to project a second image of the at least one object onto the sensor. The on-tool measurement system includes a sensor configured to capture the first and second images and a controller configured to measure differential displacements between the first and second images at each deflection element position and to calculate the optical setup local WF gradients that depend on the measured differential displacements.

In yet another aspect, an inspection system is provided. The inspection system includes an illumination unit comprising at least one light source, a collection unit that includes at least one light detector, a control unit that includes at least one processor, and an optical setup that includes a moveable deflection element further comprising a highly transparent region. The deflection element includes a first surface configured to project a first image of at least one object onto a sensor and the highly transparent region includes a second surface configured to project a second image of the at least one object onto the sensor. The inspection system includes a sensor configured to capture the first and second images of the at least one object wherein the at least one processor is configured to measure differential displacements between the first and second images at each moveable deflection element position, and to calculate local WF gradients that depend on the differential displacements.

In another aspect, an on-tool wavefront (WF) aberration measurement method is provided. The method includes illuminating a specimen, by a light source, the specimen includes at least one object on its surface, moving a deflection element across a pupil plane of an optical setup, by a controller, the moveable deflection element having a highly transparent region, the moveable deflection element includes a first surface configured to project a first image of the at least one object onto a sensor and the highly transparent region comprises a second surface configured to project a second image of the at least one object onto the sensor. The method includes capturing the first and second images, by the sensor, for each aperture position, measuring differential displacements between the first and second images at each moveable deflection element, and calculating local WF gradients that depend on the measured displacements.

In yet another aspect, a computer program product for measuring optical system's wavefront (WF) aberrations is provided. The computer program product may include first program instructions to measure differential displacements between a first and a second images and second program instructions to calculate local WF gradients that depend on the measured differential displacements. The computer program product may include third program instructions to calculate WFs from the measured local WF gradients. The computer program product may include fourth program instructions to calculate the slope of the intensity of the second image and to correct de-focus aberrations in the calculated WFs by correcting the measured differential displacements using a pre-defined conversion table. The computer program product may include fifth program instructions to monitor WF aberrations of the optical setup routinely.

Numerous other aspects are provided in accordance with these and other embodiments of the invention. Other features and aspects of embodiments of the present invention will become more fully apparent from the following detailed description, the appended claims, and the accompanying drawings.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION

The following detailed description is of exemplary embodiments of the invention but the invention is not limited thereto, as modifications and supplemental structures may be added, as would be apparent to those skilled in the art. In particular, but without limitation, while an exemplary embodiment may be disclosed with regard to the inspection of a specimen that may be a photomask, a reticle or a wafer, it would be readily apparent to one skilled in the art that the teachings are readily adaptable to semiconductor photolithography stepper tools. While an on-tool measurement system for measuring WF aberrations of inspection tools' optical system is depicted and described in details herein below, the principles of the present invention are applicable to both types of semiconductor process tools and systems. As would be understood by one skilled in the art, both types of systems may be utilized in accordance with the present invention.

The principles of the present invention are applicable to any optical system of any microscope, and semiconductor process tools are depicted and described in details herein below as non-limiting example of such devices' optical systems.

As used herein, the words "photomask", "mask" and "reticle" are interchangeable and mean an opaque plate with holes or transparencies configured to allow light to shine through in a defined pattern.

In the description and claims of the application, each of the words "comprise" "include" and "have", and forms thereof, are not necessarily limited to members in a list with which the words may be associated.

The on-tool WF aberrations measurement system, method and computer product disclosed herein address the above stated need for measuring WF aberrations of semiconductor process tools' optical systems and aim to increase process yields and reliability of semiconductor process inspection tools and steppers.

According to an aspect of some embodiments of the present invention, there is provided an on-tool measurement system for measuring optical system's WF aberrations. The on-tool measurement system includes an optical setup comprising a moveable deflection element further comprising a highly transparent region. The deflection element includes a first surface configured to project a first image onto a sensor and the highly transparent region includes a second surface configured to project a second image onto the sensor. The moveable deflection element may be a wedge, the highly transparent region may be a vacant aperture and the second surface may be the cross section of the vacant aperture. Optionally, the highly transparent region may include highly transparent material that includes the second surface having a different angle relative to the wedge angle.

The on-tool WF aberrations measurement system includes a sensor configured to capture the first and second images and a controller configured to measure differential displacements between the captured first and second images at each deflection element position. According to embodiments of the present invention, the differential displacements depend on the optical system's local WF gradients.

On-tool WF aberrations measurement system's moveable deflection element may be configured to compensate for both de-focus aberrations along the Z axis (in perpendicular direction to the specimen X-Y plane) and jitter aberrations in the specimen X-Y plane providing an accurate method for measuring WF aberrations and accordingly calculating WFs of optical systems.

Optionally, the on-tool measurement system's controller may be configured to calculate WFs for a plurality of locations in a FOV based on measured differential displacements. The plurality of locations in a FOV is projected by the optical setup to a plurality of images through various regions of the optical setup onto the sensor (or a plurality of sensors), generating location dependent differential displacements. WFs may be calculated by calculating the Zernike polynomials coefficients or by any other representation known in the art.

According to another aspect of some embodiments of the present invention, an inspection system is disclosed. The inspection system includes an illumination unit comprising at least one light source, a collection unit comprising at least one light detector, a control unit comprising at least one processor and an optical setup. The optical setup includes a moveable deflection element further comprising a highly transparent region. The deflection element includes a first surface configured to project a first image onto a sensor and the highly transparent region includes a second surface configured to project a second image onto the sensor or a plurality of sensors.

The inspection system includes a sensor configured to capture the first and second images wherein a processor is configured to measure differential displacements between the first and second images at each moveable deflection element position, and to calculate local WF gradients that depend on the measured differential displacements.

It should be noted that linear dependence of the local WF gradients on measured displacements may be assumed. However, embodiments of the present invention are not limited to linear dependence and may utilize non-linear dependence as well using formulas, conversion tables and the like.

Figure 1:
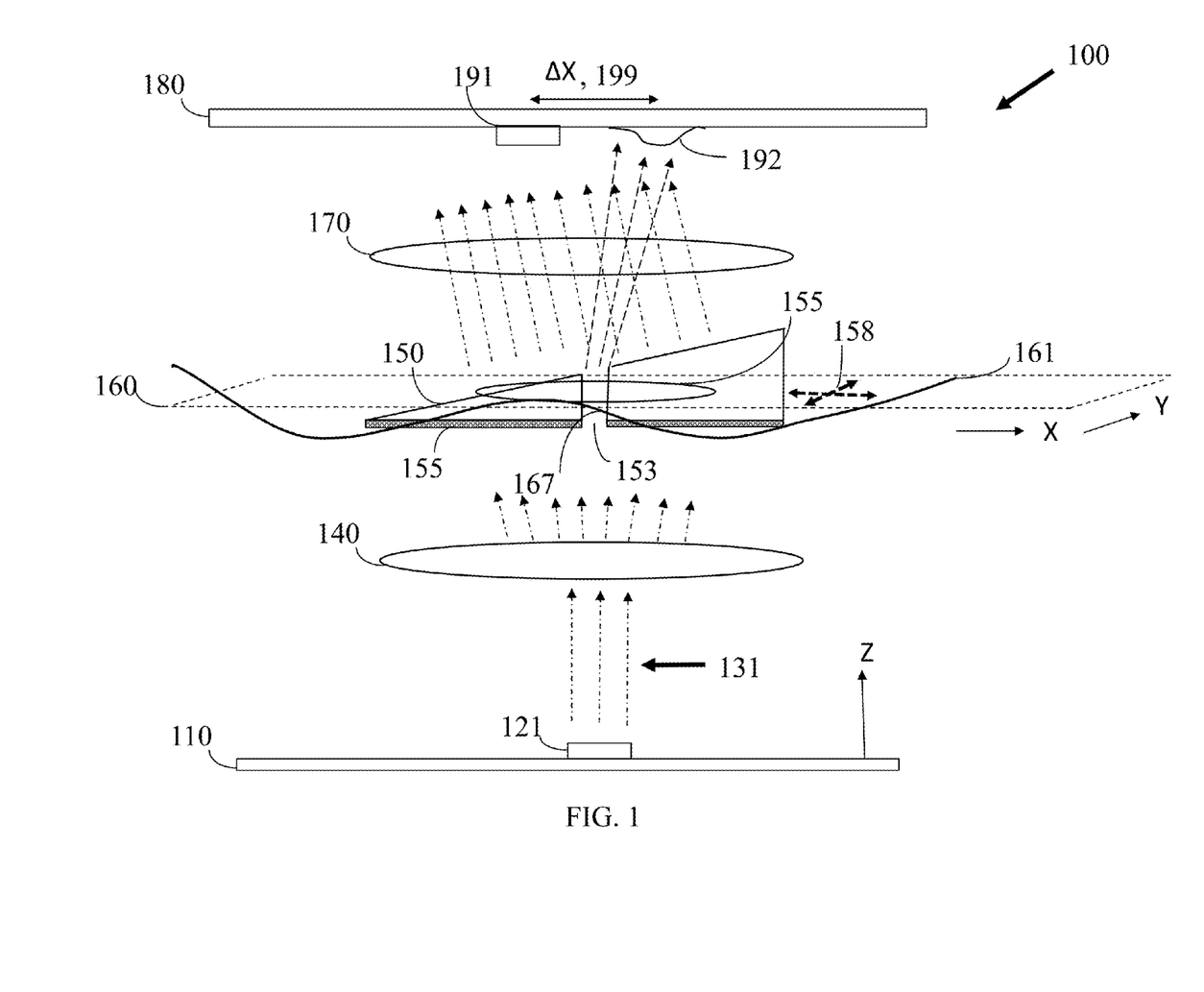
FIG. 1 illustrates an on-tool measurement system for measuring WF aberrations of an optical system, according to certain embodiments.

Reference is now made to FIG. 1, which illustrates an on-tool measurement system 100 for measuring WF aberrations of an optical system, according to certain embodiments. On-tool measurement system 100 for measuring WF aberrations of an optical system may include a specimen 110 that may be a photomask, reticle or a wafer. Specimen 110 may include at least one object 121 that may be a contact hole that reflects or transmits a beam of light 131. A first lens 140 may be configured to convert spherical waves to plane waves and a second lens 170 may be configured to focus light beams onto a sensor plane 180. Additional optical elements (not shown) may be used and optical lenses 140 and 170 represent such optical elements that may be included in the optical setup and are known in the art.

According to embodiments of the present invention, on-tool measurement system 100 includes a moveable deflection element 150 having highly transparent region 153 located at a pupil 155 in a pupil plane 160 of optical system 100.

Optionally, moveable deflection element 150 may be a wedge that includes a bottom and a top surface. The top surface may be tilted by an angle θ (156 shown in FIG. 4) relative to the bottom surface. Moveable wedge element 150 is configured to tilt incoming light rays by the angle θ, where θ may be typically in the range of about 1 to 30 degrees and preferably in the range of about 2 to 5 degrees.

It should be noted that according to embodiments of the present invention, the value of the angle θ, which is configured to tilt and separate between first image 191 and second image 192, may be varied between different inspection systems and inspected specimens. Accordingly, different moveable deflection elements 150 having various θ values may be utilized for different inspected specimens adapted to the characteristic distances between objects on the inspected specimen for example.

Optionally, moveable deflection element 150 may include an attenuation layer 155 configured to dim the intensity of first image 191 projected by moveable deflection element 150 onto sensor plane 180. Attenuation layer 155 may be a bottom layer or a top layer deposited onto the wedge element 150 surfaces comprising any partially transmitting material known in the art.

Optionally, highly transparent region 153 may be an aperture, wherein the aperture's area may typically occupy a small fraction of about 0.1% to 10% of moveable deflection element 150 surface area and preferably about 2% to 3% of its surface area.

It should be noted that first image 191 is generated by light rays transmitted through the full surface area of moveable deflection element 150 while second image 192 is generated by light rays transmitted mostly through highly transparent region 153. Due to attenuation layer 155, first image 191, generated by light rays transmitted through the full surface area of moveable deflection element 150, is dimmed such that its intensity is substantially equal to the intensity of second image 192.

Second image 192, projected by or through highly transparent region 153 is a smeared image of object 121 comparing to first image 191 which is sharper since it is formed by light rays transmitted by moveable deflection element 150 full surface area.

Note that highly transparent region 153 may be a vacant aperture or may comprise any highly transparent material known in the art, where the highly transparent material top surface angle (not shown) is different from moveable deflection element 150 top surface angle θ.

According to embodiments of the present invention, deflection element 150 may be used without attenuation layer 155.

A controller (not shown), or any other processor included in the system, is configured to move wedge element 150 across pupil plane 160 in the X and Y directions 158. Moveable deflection element 150 is configured to project a first image 191 of object 121 onto sensor 180 and highly transparent region 153 is configured to project a second image 192 onto sensor plane 180. The controller may be configured to measure the displacement $\Delta X$ 199 (and a second component $\Delta Y$ not shown), between the first image 191 and the second image 192 centers at the sensor plane 180 for each moveable deflection element 150 position.

The measured displacement $\Delta X$ 199 (and $\Delta Y$) between the first and second images, 191 and 192, depends on and generated by the optical system's local WF gradient 167 at the pupil plane 160 as illustrated by WF 161. It should be noted that an ideal optical system is expected to have a perfect planar WF and that with an ideal optical system WF 161 should have been illustrated by a straight line in the pupil plane 160.

Typically, the measured differential displacements depend linearly on the optical system's local WF gradients and the controller is configured to calculate the WF local gradients using a linear formula. However, non-linear dependence may also be taken into account by the controller.

Optionally, the controller (not shown), or other processor included in the system, may be configured to calculate the complete WF across the pupil plane from the calculated local WF gradients in each moveable deflection element 150 position. The calculated WF may depend also on the FOV and thus the calculation may be performed for a plurality of FOVs generating a plurality of calculated WFs.

According to embodiments of the present invention, the moveable deflection element 150 is configured to reduce the system jitter in the X-Y plane. The jitter reduction is achieved by the displacement measurement, which is differential, and hence movements of both images are subtracted and do not reduce the accuracy of the calculation. It should be noted that the inventors have realized that the information required for the local WF aberrations calculation is the location of second image 192 projected via highly transparent region 153 and that first image 191 projected via the full moveable deflection element 150 is used as a jitter cancelling reference.

According to embodiments of the present invention, the on-tool measurement system's sensor may be one or more charge-coupled device (CCD) sensor camera, complementary metal-oxide-semiconductor (CMOS) sensor camera or photomultiplier detector (PMT).

Optionally, the moveable deflection element 150 may be shifted by a controller from the optical path after the WF aberrations are measured.

Figure 2:
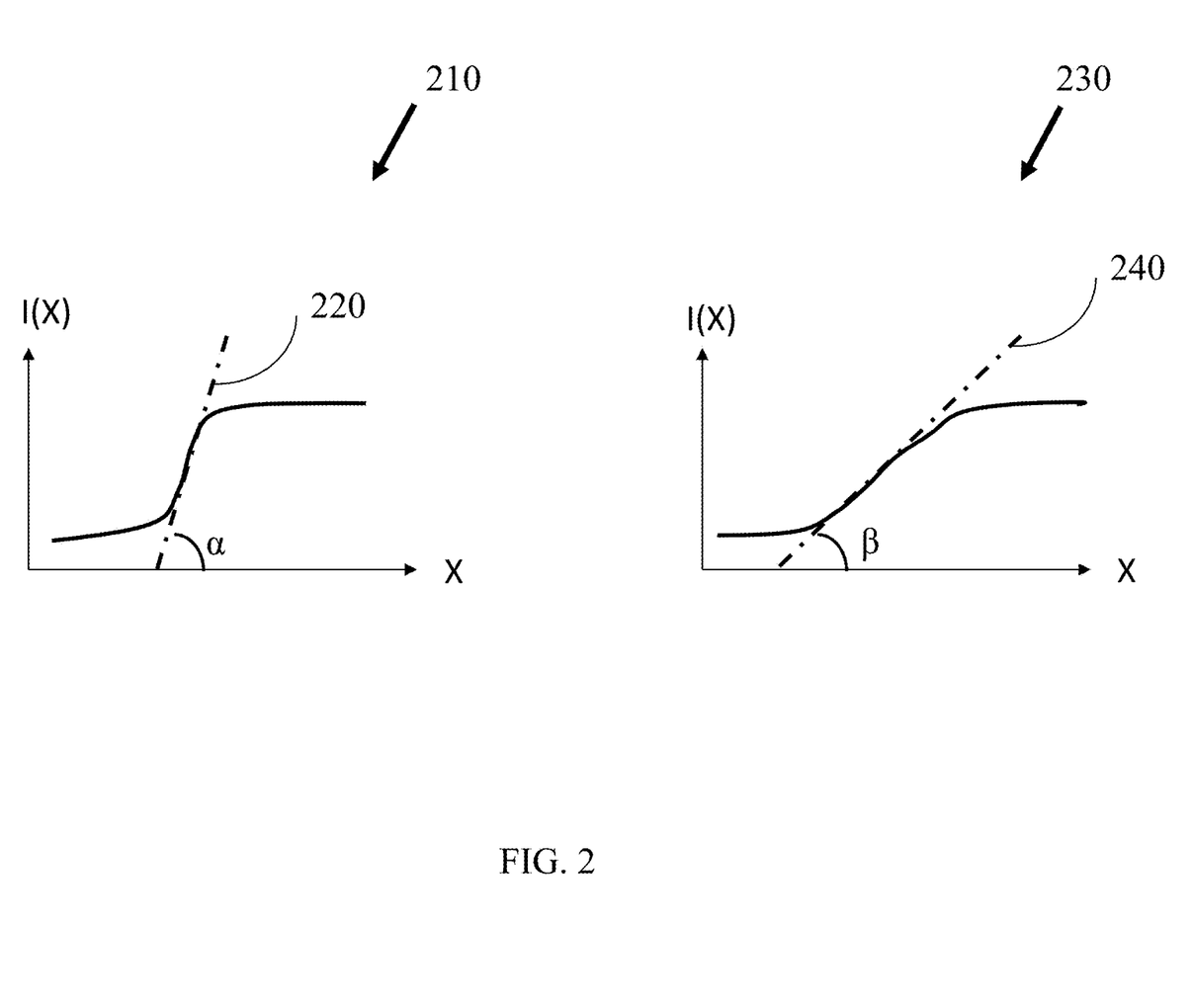
FIG. 2 illustrates image intensities along the X axis in focus and out of focus, according to certain embodiments.

Reference is now made to FIG. 2, which illustrates image intensities along the X axis in focus 210 and out of focus 230, according to certain embodiments.

The captured image intensity along the X axis is shown. The slope of the captured intensity curve 220, has an angle α which is bigger than the slope of the second, out of focus, intensity curve 240 having an angle β. As illustrated in FIG. 2, α is bigger than β, which means that the gradient of the cross-section 210 is better than the gradient of the cross-section 230. The improved contrast of intensity curve 210 is due to a better positioning, in focus, of the inspected specimen in the perpendicular direction normal to the specimen plane along the Z axis.

According to embodiments of the present invention, a controller (not shown) may be configured to calculate the slope of the intensity of the second image and to correct the measured differential displacements between first image 191 and second image 192 (shown in FIG. 1), using a pre-defined conversion table (not shown).

As shown, the on-tool moveable deflection element 150 enables correcting both de-focus aberrations along the Z axis and jitter aberration in the specimen X-Y plane providing an accurate method for measuring WF aberrations of optical systems.

Figure 3:
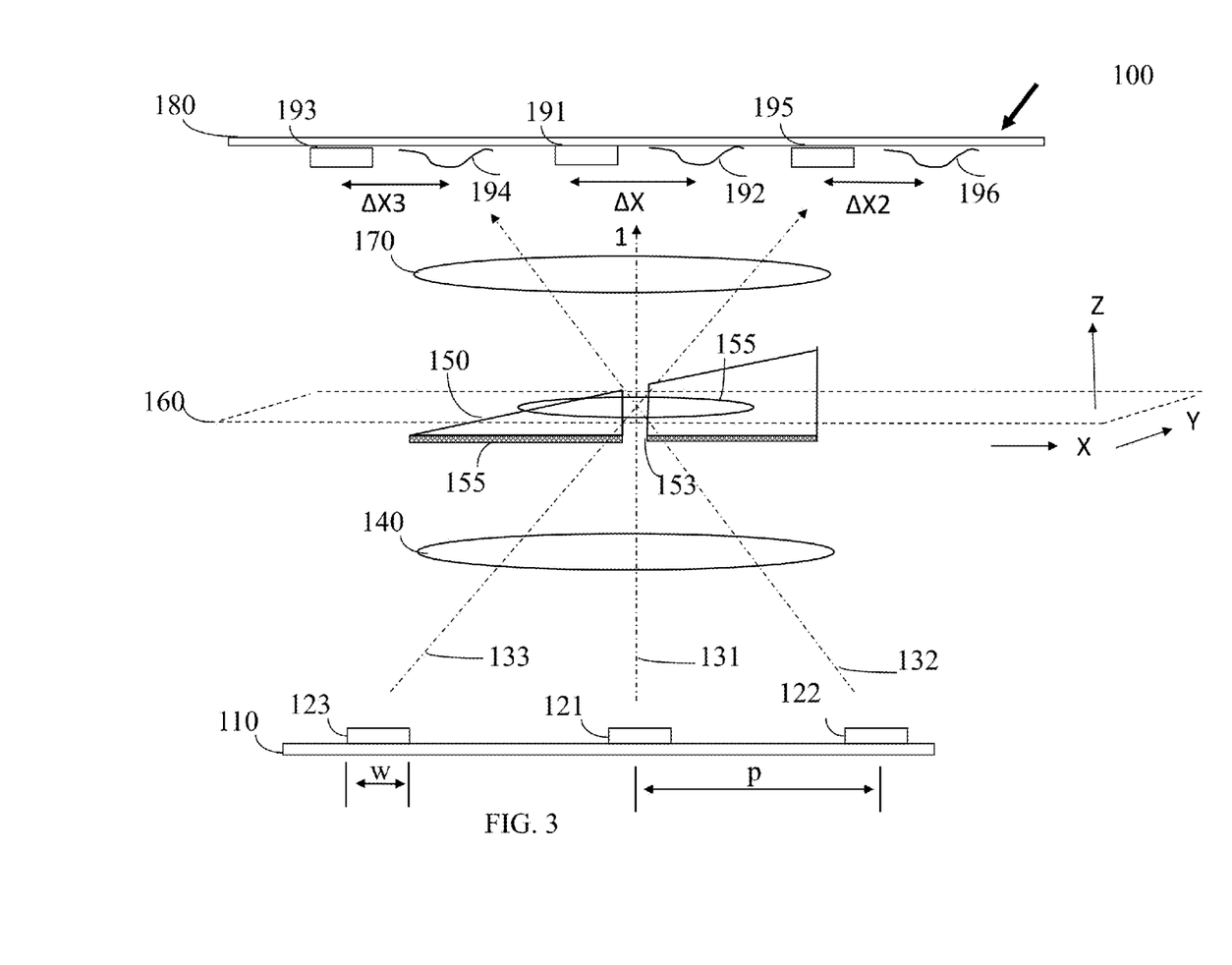
FIG. 3 illustrates the on-tool measurement system for measuring WF aberrations of an optical system with three objects on the specimen surface, according to certain embodiments.
Figure 4:
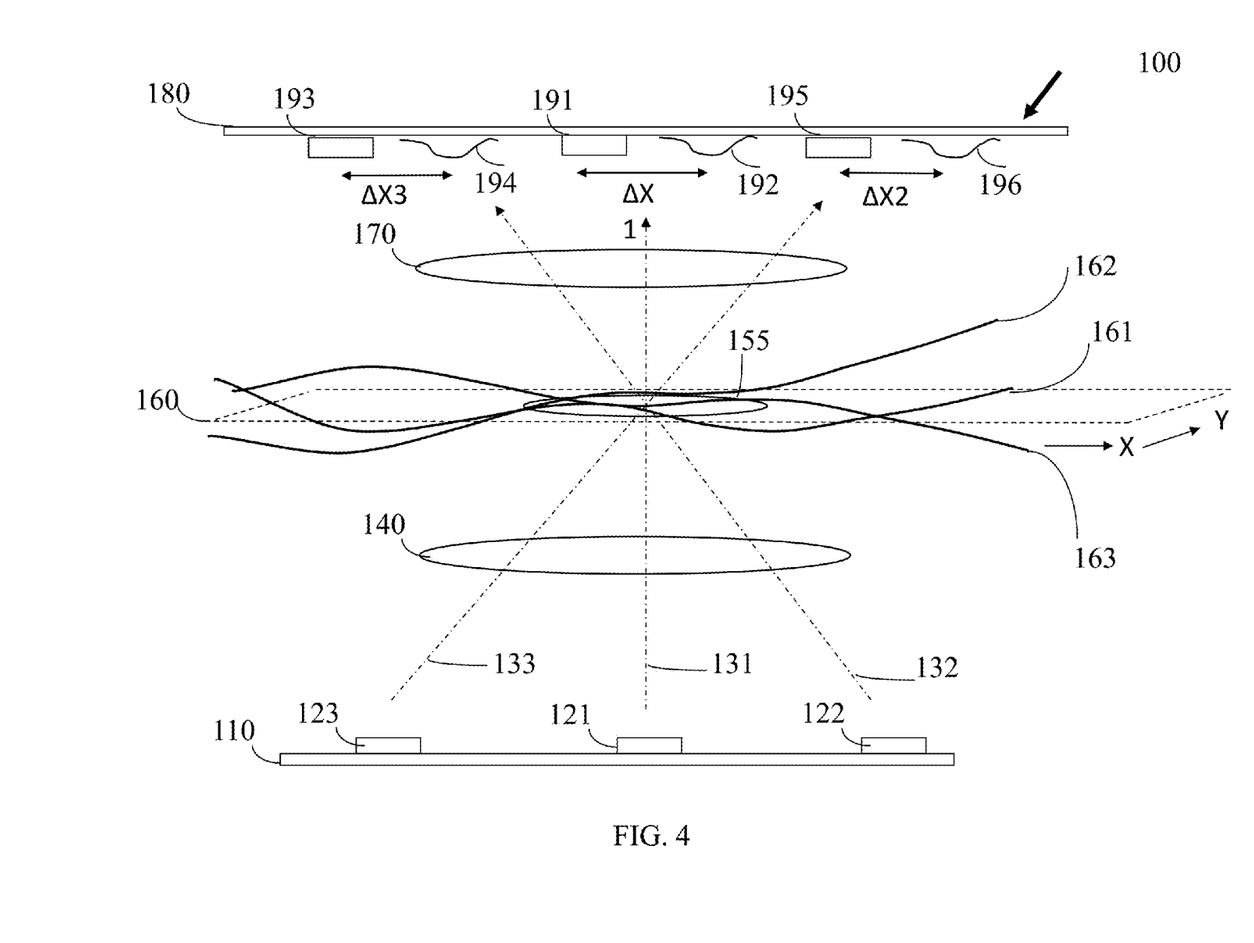
FIG. 4 illustrates three exemplary WF surfaces of the optical system originating from three locations in a field of view (FOV), according to certain embodiments.

Reference is now made to FIG. 3, which illustrates on-tool measurement system 100 for measuring WF aberrations of an optical setup having three objects 121, 122 and 123 deployed on the specimen 110 surface, according to certain embodiments. Optionally, the three contact holes 121, 122 and 123 may have similar widths and pitch distances between adjacent holes. On-tool measurement system 100 may use specimen 110 having a plurality of contact holes, such as contact holes 121, 122 and 123, in order to measure and calculate WFs 161, 162 and 163 in multiple positions on specimen 110 concurrently as illustrated in FIG. 4. Optionally, specimen 110 may include a two dimensional array of contact holes as illustrated further below in FIG. 5. However, other number of contact holes, other contact holes arrangements and/or other objects and other object shapes may be deployed on specimen 110 and such other arrangements and/or objects and/or object shapes are in the scope.

On-tool measurement system 100 moveable deflection element 150 is configured to project a first image 191 of object 121 onto sensor 180 and highly transparent region 153 is configured to project a second image 192 onto sensor 180 illustrated by dashed arrows 131. Moveable deflection element 150 projects a first image 193 of object 122 onto sensor 180 and highly transparent region 153 projects a second image 194 onto sensor 180 illustrated by a dashed arrow 132. Moveable deflection element 150 projects a first image 195 of object 123 onto sensor 180 and highly transparent region 153 projects a second image 196 onto sensor 180 illustrated by a dashed arrow 133.

On-tool measurement system 100 controller (not shown) may be configured to calculate WFs originating from the exemplary three objects 121, 122 and 123 using the measured differential displacements ΔX1, ΔX2 and ΔX3. ΔX1, ΔX2 and ΔX3 may have similar or different values that depend on the optical system local WF gradients seen from each object 121, 122 and 123 FOV as illustrated in FIG. 3.

Reference is now made to FIG. 4, which illustrates three exemplary WF surfaces 161, 162 and 163 of the optical system originating from three locations in the FOV, according to certain embodiments. Light rays reflected or transmitted from each object 121, 122 and 123 pass substantially through different regions of the optical setup designated by dashed arrows 131, 132 and 133. Hence, the WF aberrations measured and calculated for each location in the FOV may vary as illustrated by WFs 161, 162 and 163 and hence may generate different values of image displacement ΔX1, ΔX2 and ΔX3.

It should be noted that the measured image displacement values ΔX1, ΔX2 and ΔX3 depend on the local WF gradients at the highly transparent region 153 and that for each position of moveable deflection element 150 at the pupil plane different differential displacements ΔX1, ΔX2 and ΔX3 (and ΔY1, ΔY2 and ΔY3 not shown) may be measured generated by the different local WF gradients.

Furthermore, it should be noted that the first and second images are projected onto 2 dimensional sensor plane 180 and hence the measured differential displacements may have two independent components, ΔX and ΔY, as illustrated further below in FIGS. 5, 6 and 7.

Figure 5:
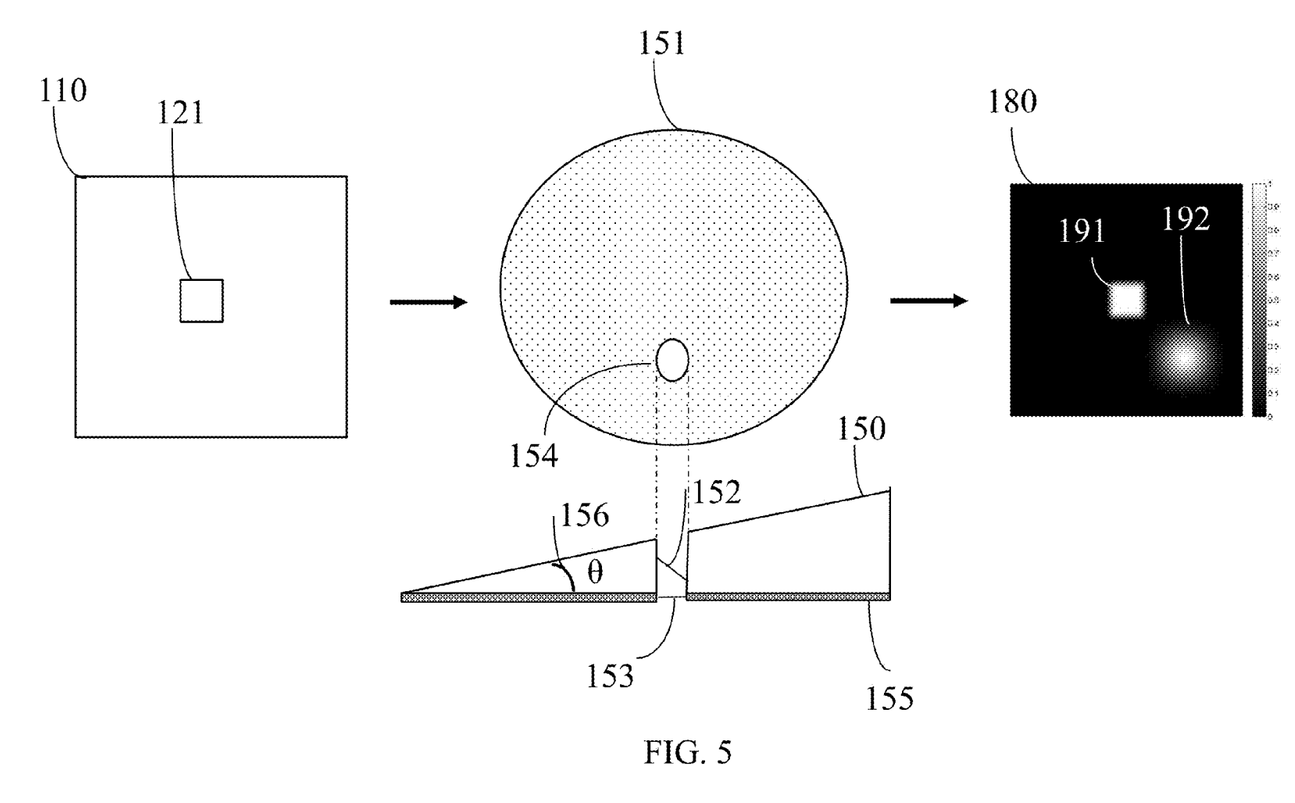
FIG. 5 illustrates how the two images shown in FIG. 1 are created and projected onto the sensor plane by the moveable deflection element and the highly transparent region, according to certain embodiments.

Reference is now made to FIG. 5, which illustrates how the two images illustrated in FIGS. 1, 191 and 192, are created and projected onto sensor plane 180 by moveable deflection element 150 and the highly transparent region 153, according to certain embodiments.

Light rays reflected or transmitted through object 121 deployed on specimen surface 110, illustrated on the left side of FIG. 5, are transmitted through the full surface of moveable deflection element 151 and through aperture 154, illustrated on the center of FIG. 5, and generate two images on sensor plane 180, illustrated on the right side of FIG. 5.

Moveable deflection element 150 that may be a wedge is illustrated in a side view cross section 150. Moveable deflection element 150 includes a highly transparent region 153 that may be a vacant aperture or may include a highly transparent material having a top surface 152 having a different angle relative to wedge angle θ 156.

Additionally, moveable deflection element 150 is illustrated in a top view 151 that shows its circular shape and the circular shape of the aperture 154. A first image 191 is projected through the full moveable deflection element surface and body. First image 191 is a sharp and high intensity image, which is dimmed by attenuation layer 155. First image 191 position at the sensor plane 180 depends substantially on the moveable deflection element angle θ 156 and is insensitive to the WF aberrations that are averaged over the area of the moveable deflection element 150. The first image 191 may be dimmed by partially transparent layer 155 illustrated also by the dashed area shown in moveable deflection element 151 surface for this purpose.

Second image 192 projected onto sensor plane 180 is generated by light rays that pass substantially through aperture 154 and is a smeared image insensitive to the wedge angle θ

156. The displacement between the two images in the two dimensional sensor plane 180, depicted in FIG. 5 by ΔX and ΔY, depend on the local WF gradients at aperture position 154.

The differential displacements, ΔX and ΔY, may be calculated by the controller as the distance between the centers of images 191 and 192. The centers of the images may be calculated by detecting the locations of the image edges or by calculating the center of mass of an image in terms of light intensity.

Figure 6:
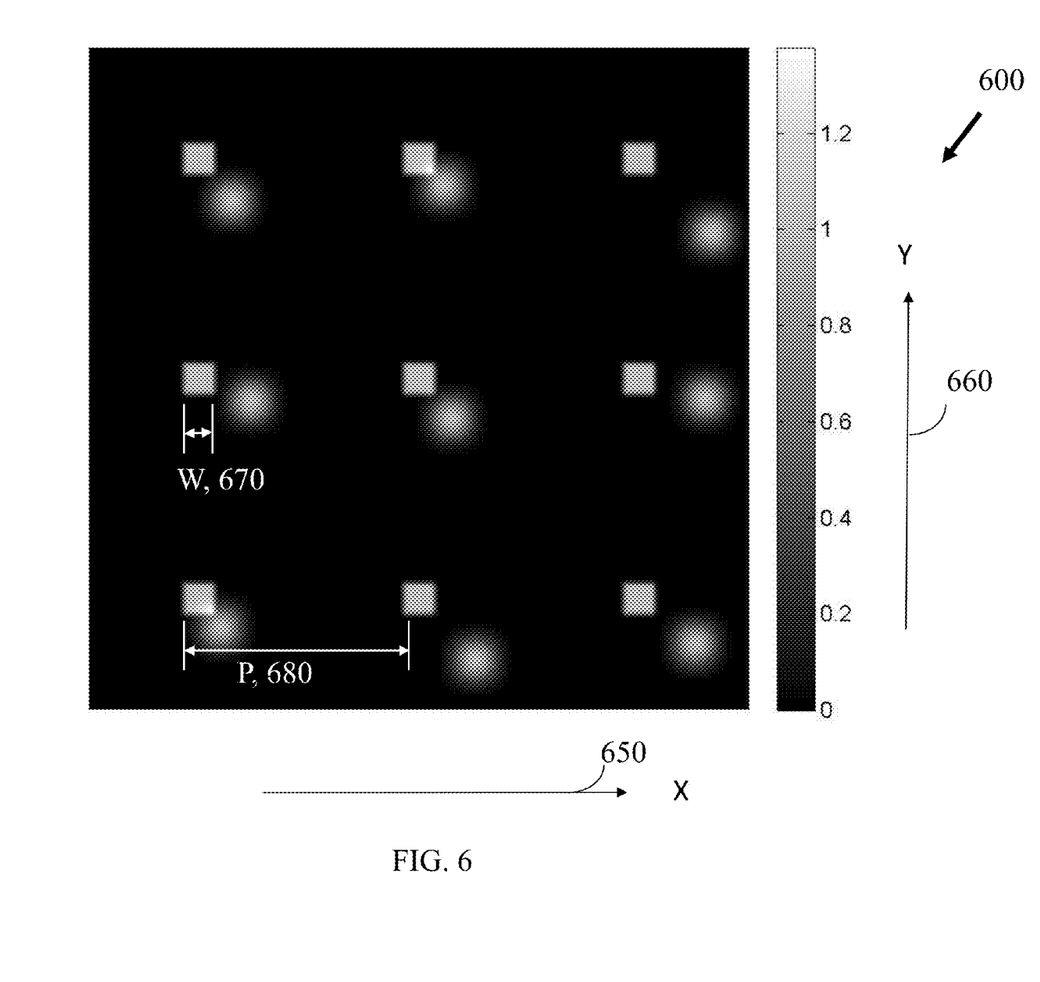
FIG. 6 illustrates an exemplary two dimensional array of features deployed on a specimen surface, according to certain embodiments.

Reference is now made to FIG. 6, which illustrates an exemplary two dimensional array 600 of features that may be contact holes (CHs) deployed on specimen surface 110, according to certain embodiments. Specimen 110 illustrated in the X 650 and Y 660 plane may include a two dimensional array of CHs having, for example, a constant width, W 670, and constant pitch between adjacent CHs P 680. A three by three array of CHs is illustrated in FIG. 6, however, other number of CH's may be used in a two dimensional array. The shape of the illustrated CHs is cubical, however other, non-cubical, CH shapes with various widths and heights for example may be envisaged and are in the scope. It should be noted that CHs widths and distance between CHs may not be fixed values and that FIG. 6's two dimensional array of CHs illustration is a non-limiting example.

According to embodiments of the present invention, specimen 110 having a two dimensional array of CHs 600, or any other objects arrangement, may be a member of on-tool measurement system 100 (not shown) used to measure the optical system WF aberrations routinely. According to embodiments of the present invention, the WF aberration measurement and WF calculation may be routinely repeated with specimen 110 during the tool lifetime to assure that the optical system performance was not degraded for example due to optical system elements failure or other failures that might affect the optical system performance. However, it should be noted that the WF aberration measurement and WF calculation may be performed with other specimens, for example with an inspected specimen and is not limited and not specific to a unique specimen 110 structure and content.

Figure 7:
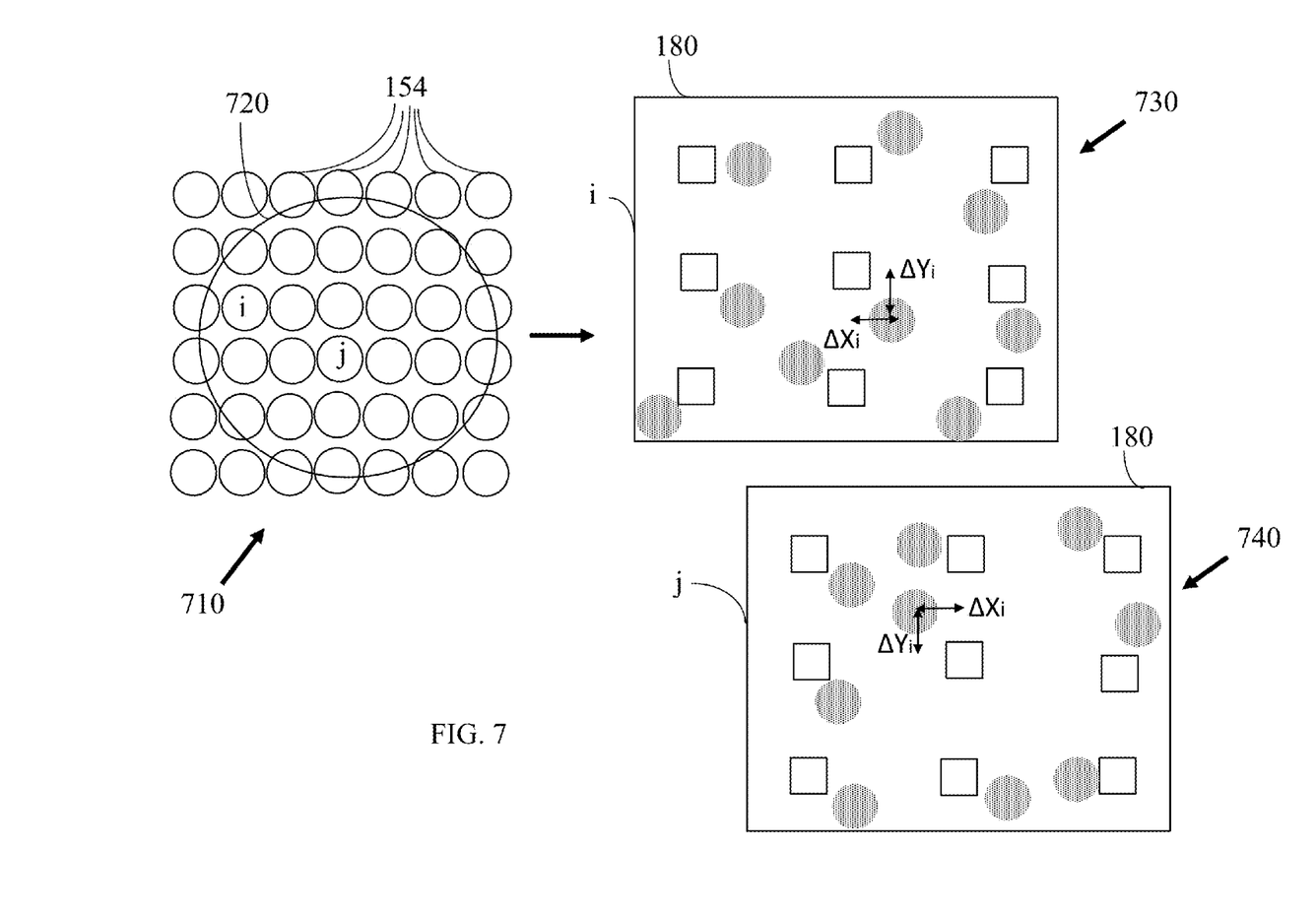
FIG. 7 illustrates pluralities of images and image displacements captured by the sensor at two deflection element positions, according to certain embodiments.

Reference is now made to FIG. 7, which illustrates pluralities of images and differential displacements captured by the sensor at two deflection element positions, according to certain embodiments. On the left side of FIG. 7, 710, the pupil area 720 is illustrated covered schematically by a plurality of deflection element's highly transparent region positions 154 obtained by shifting the moveable deflection element (not shown) by a processor (not shown).

For example, two positions i and j are designated on the left side FIG. 710, and their resulting captured images on the sensor plane 180 are illustrated in two separate images on the right side of FIGS. 7, 730 (i) and 740 (j). The differential displacements, ΔXs and ΔYs, between a plurality of first images, illustrated by dashed area, and a plurality of second images, illustrated by vacant rectangles, vary between images 730 and 740. The differential displacements may vary also between adjacent object images as illustrated in images 730 and 740 where the second image smeared circles are scattered relative to the first image sharp vacant rectangles in the X and Y directions.

Figure 8:
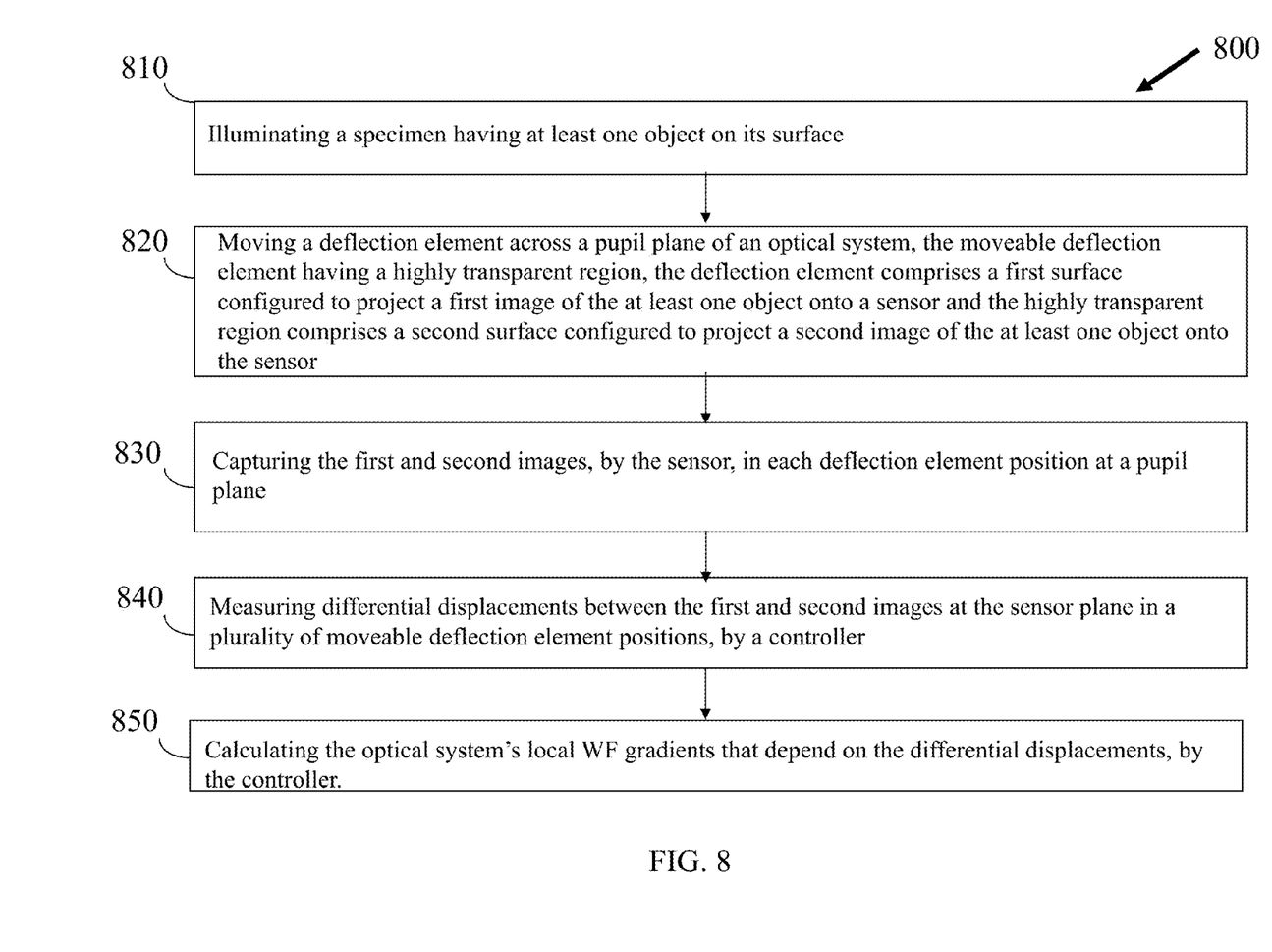
FIG. 8 illustrates a flowchart of an on-tool measurement method for measuring WF aberrations of an optical system, according to certain embodiments.

Reference is now made to FIG. 8, which illustrates a flow-chart of an on-tool measurement method for measuring WF aberrations of an optical system, according to certain embodiments. Method 800 for measuring WF aberrations may include: in stage 810, illuminating a specimen comprising at least one object deployed on its surface; in stage 820, moving a deflection element across a pupil plane of an optical system, the moveable deflection element having a highly transparent region, the moveable deflection element includes a first surface configured to project a first image of the at least one object onto a sensor and the highly transparent region includes a second surface configured to project a second image of the at least one object onto the sensor; in stage 830, capturing the first and second images, by the sensor, in each moveable deflection element position; in stage 840, measuring differential displacements between the first and second images in a plurality of moveable deflection element positions, by a controller; and in stage 850, calculating optical system's local WF gradients that depend on the measured differential displacements.

Method 800, stage 850 may include calculating local WF gradients assuming a linear dependence of the local WF gradients on the measured differential displacements.

Optionally, method 800 for measuring WF aberrations may include calculating WFs for a plurality of locations in a FOV.

Optionally, method 800 for measuring WF aberrations may include calculating the slope of the intensity of the first image and correcting de-focus aberrations in the calculated WFs by correcting the measured differential displacements using a pre-defined conversion table.

According to a further feature of an embodiment of the present invention, the controller may be configured to compensate for the measured WF aberrations. The WF aberrations compensation may be performed by a computer program executed by a processor configured to take into account the measured WF aberrations during die-to-die or cell-to-cell comparisons.

Additionally or alternatively, WF aberrations compensation may be performed using adaptive hardware managed by a computer program executed by a processor, wherein the adaptive hardware may include an adaptive lens and the like.

According to a further feature of an embodiment of the present invention, the controller, configured to measure WF aberrations and compensate for WF aberrations, may be operated iteratively, in a close loop, where for example in a second iteration, the WF aberrations may be re-measured and re-calculated again after the first iteration compensation is performed, and perform further a second compensation using the die-to-die or cell-to-cell comparison computer program or an adaptive lens as described herein above. If needed, a third, fourth, fifth or any number of such iterations may be performed in a close loop until a pre-defined convergence criterion may be achieved.

It should be noted that according to embodiments of the present invention, measuring the optical system WF aberrations may improve the inspection system detection stability, repeatability and reliability in addition to improving the detection performance and resolution.

According to a further feature of an embodiment of the present invention, a computer program product for on-tool WF aberrations measurement of an optical setup is disclosed. It should be understood that each block of the flowchart illustrations and/or block diagrams, and combinations of blocks in the flowchart illustrations and/or block diagrams, can be implemented by computer program instructions. These computer program instructions may be provided to a processor and create means for implementing the functions specified in the flowcharts and block diagrams.

The computer program instructions may also be stored in a computer readable medium that can direct a computer or other systems to function in a particular manner, such that the instructions stored in the computer readable medium produce an article of manufacture including instructions which implement the function specified in the flowcharts and block diagrams.

The computer program product may include first program instructions to measure differential displacements between a first and a second images and second program instructions to calculate local WF gradients that depend on the measured differential displacements. The computer program product may include third program instructions to calculate WFs from the measured local WF gradients.

The computer program product may include fourth program instructions to calculate the slope of the intensity of the second image and to correct de-focus aberrations in the calculated WFs by correcting the measured differential displacements using a pre-defined conversion table.

The computer program product may include fifth program instructions to monitor WF aberrations of the optical setup routinely.

Advantageously, the above described on-tool measurement system for measuring WF aberrations is configured to correct de-focus and jitter aberrations by differential displacements measurement and to provide a set of WF aberrations of an optical system using a moveable deflection element.

Advantageously, the moveable deflection element may be a wedge, where the wedge angle $\theta$ may be typically in the range of about 1 to 30 degrees, and where $\theta$ determines the tilt of a first image in the sensor plane.

Another advantage of the above described on-tool measurement system for measuring WF aberrations is that the moveable deflection element may be shifted by a controller from the optical path after the WF aberrations are measured.

Another advantage of the above described on-tool measurement system for measuring WF aberrations is that WFs may be calculated for a plurality of locations in a FOV based on the measured local WF gradients.

Another advantage of the above described on-tool measurement system for measuring WF aberrations is that it may include an on-tool specimen specifically designed for WF aberrations measurement. The on-tool specimen may be used routinely to assure that the optical system's performance did not degrade and that the inspection system allows differentiating between true defects and false defects reliably.

Another advantage of the above described on-tool measurement system for measuring WF aberrations is that monitoring routinely the optical system's performance of semiconductor process stepper tools may prevent generating systematic defects and yield reduction due to the optical system's WF aberrations.

Another advantage of the above described on-tool measurement system for measuring WF aberrations is that it may improve the inspection system detection stability, repeatability and reliability in addition to improving the detection performance and resolution.

While a number of exemplary aspects and embodiments have been discussed above, those of skill in the art will recognize certain modifications, permutations, additions and sub combinations thereof. It is therefore intended that the following appended claims and claims hereafter introduced be interpreted to include all such modifications, permutations, additions and sub-combinations as are within their true spirit and scope.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description. While preferred embodiments of the present invention have been shown and described, it should be understood that various alternatives, substitutions, and equivalents can be used, and the present invention should only be limited by the claims and equivalents thereof.

What is claimed is:

1. An on-tool measurement system for measuring wavefront (WF) aberrations of an optical setup, the system comprising:
    an optical setup comprising a moveable deflection element further comprising a highly transparent region, the deflection element comprises a first surface configured to project a first image of at least one object onto a sensor and the highly transparent region comprises a second surface configured to project a second image of the at least one object onto the sensor;
    a sensor configured to capture the first and second images of the at least one object; and
    a controller configured to measure differential displacements between the first and second images at each moveable deflection element position, and to calculate local WF gradients that depend on the differential displacements.

2. The system according to claim 1, wherein the moveable deflection element is configured to be shifted by a controller from the optical path after the WF aberrations are measured.

3. The system according to claim 1, wherein the moveable deflection element comprising an attenuation layer configured to dim the intensity of the first image projected by the moveable deflection element onto the sensor.

4. The system according to claim 1, wherein the highly transparent region area occupies between about 0.1% to 10% of the moveable deflection element area.

5. The system according to claim 1, wherein the moveable deflection element is a wedge, the highly transparent region is a vacant aperture and the second surface is the cross section of the vacant aperture.

6. The system according to claim 1, wherein the controller is configured to calculate WF aberrations for a plurality of locations in the field of view (FOV) based on the calculated local WF gradients.

7. The system according to claim 2, further comprising a pre-defined conversion table used to correct de-focus aberrations that affect the measured differential displacements.

8. The system according to claim 1, comprising an on-tool specimen further comprising a plurality of objects, the system is configured to monitor the optical setup performance routinely by measuring the differential displacements and calculating the local WF gradients using the on-tool specimen.

9. The system according to claim 1, wherein the differential displacements between images depend linearly on the local WF gradients.

10. The system according to claim 5, wherein the moveable wedge element comprising a bottom and a top surfaces, the top surface is tilted by an angle θ relative to the bottom surface, the wedge element is configured to tilt incoming rays by the wedge angle θ, wherein θ is in the range of about 1 to 15 degrees.

11. The system according to claim 1, wherein the sensor is selected from the group consisting of: a CCD, a CMOS and a PMT.

12. An inspection system, the system comprising:
an illumination unit comprising at least one light source;
a collection unit comprising at least one light detector;
a control unit comprising at least one processor; and
an optical setup comprising a moveable deflection element further comprising a highly transparent region, the deflection element comprises a first surface configured to project a first image of at least one object onto a sensor and the highly transparent region comprises a second surface configured to project a second image of the at least one object onto the sensor;
a sensor configured to capture the first and second images of the at least one object; and
wherein the at least one processor is configured to measure differential displacements between the first and second images at each moveable deflection element position, and to calculate local WF gradients that depend on the differential displacements.

13. An on-tool wavefront (WF) aberration measurement method, the method comprising:
illuminating a specimen, by a light source, the specimen comprising at least one object on its surface;
moving a deflection element across a pupil plane of an optical setup, by a controller, the moveable deflection element having a highly transparent region, the moveable deflection element comprises a first surface configured to project a first image of the at least one object onto a sensor and the highly transparent region comprises a second surface configured to project a second image of the at least one object onto the sensor;
capturing the first and second images, by the sensor, for each aperture position; and
measuring differential displacements between the first and second images at each moveable deflection element; and
calculating local WF gradients that depend on the measured displacements.

14. The method according to claim 13, comprising calculating WF aberrations for a plurality of locations in the FOV, the plurality of locations comprising a plurality of objects projecting a plurality of images through different regions of the optical setup onto the sensor.

15. The method according to claim 13, comprising calculating the second image intensity's slope and correcting de-focus aberrations in the calculated WFs by correcting the measured differential displacements using a pre-defined conversion table.

\* \* \* \* \*